(12) United States Patent
Fons

(10) Patent No.: US 7,325,971 B2
(45) Date of Patent: Feb. 5, 2008

(54) METHOD AND APPARATUS FOR LOCATING HYDROCARBON DEPOSITS

(76) Inventor: Lloyd C. Fons, 14410 Cindywood Dr., Houston, TX (US) 77079

( * ) Notice: Subject to any disclaimer, the term of this patent is extended or adjusted under 35 U.S.C. 154(b) by 0 days.

(21) Appl. No.: 11/136,975

(22) Filed: May 25, 2005

(65) Prior Publication Data

US 2006/0268957 A1    Nov. 30, 2006

(51) Int. Cl.
*G01K 13/00* (2006.01)
*G01K 3/08* (2006.01)
*G01N 25/00* (2006.01)

(52) U.S. Cl. ............... 374/136; 374/129; 374/137; 374/45; 702/16

(58) Field of Classification Search ............... 374/136, 374/128, 126, 9, 133
See application file for complete search history.

(56) References Cited

U.S. PATENT DOCUMENTS

| | | | |
|---|---|---|---|
| 2,394,703 A * | 2/1946 | Lipson ........................ 250/255 |
| 3,351,936 A * | 11/1967 | Feder ........................... 342/22 |
| 4,476,716 A | 10/1984 | Fons | |
| 4,703,175 A * | 10/1987 | Salour et al. ................. 356/45 |
| 4,884,896 A * | 12/1989 | Conway ........................ 374/9 |
| 5,165,796 A * | 11/1992 | Gat et al. .................... 374/128 |
| 5,244,483 A | 9/1993 | Brosch et al. | |
| 5,255,286 A * | 10/1993 | Moslehi et al. ............. 374/121 |
| 5,271,084 A * | 12/1993 | Vandenabeele et al. ..... 392/416 |
| 5,276,327 A * | 1/1994 | Bossen et al. ......... 250/339.09 |
| 5,281,024 A | 1/1994 | Fons | |
| 5,326,172 A * | 7/1994 | Ng .............................. 374/126 |
| 5,369,278 A * | 11/1994 | Lehto ......................... 250/343 |
| 5,743,642 A | 4/1998 | Fons | |
| 5,964,530 A | 10/1999 | Fons | |
| 6,267,501 B1 * | 7/2001 | Wand et al. ................ 374/124 |
| 6,798,341 B1 * | 9/2004 | Eckel et al. ................ 340/521 |
| 6,937,938 B2 * | 8/2005 | Sansone ...................... 702/16 |
| 7,056,011 B2 * | 6/2006 | Pesach ......................... 374/43 |
| 2005/0276308 A1* | 12/2005 | Pint ........................... 374/121 |

FOREIGN PATENT DOCUMENTS

| JP | 55131751 A * | 10/1980 |
|---|---|---|
| JP | 58135940 A * | 8/1983 |

* cited by examiner

*Primary Examiner*—Gail Verbitsky
(74) *Attorney, Agent, or Firm*—Browning Bushman P.C.

(57) ABSTRACT

A method and apparatus for locating hydrocarbon deposits includes temperature 16 sensor for measuring earth surface temperature at each of a plurality of locations, and a solar absorption sensor 14 for measuring the absorption coefficient of the earth's surface at each of those plurality of locations. A sky temperature sensor 18 may also be provided. A computer 30 records measurements as a function of location, and outputs a plot of corrected surface temperatures as a function of the geographic location of the measurements. By comparing corrected surface temperature measurements at the plurality of locations, a hydrocarbon deposit may be located and its boundaries determined.

20 Claims, 1 Drawing Sheet

METHOD AND APPARATUS FOR LOCATING HYDROCARBON DEPOSITS

FIELD OF THE INVENTION

The present invention relates to methods and apparatus for locating hydrocarbon deposits, such as oil or gas deposits, beneath the earth surface. More particularly, this invention involves measuring the earth surface temperature at each of a plurality of locations, measuring the absorption coefficient of the earth surface at each of the plurality of locations, and generating temperature profiles for determining the location of subterranean hydrocarbon deposits.

BACKGROUND OF THE INVENTION

It is vital that cost effective techniques be used to determine the most likely location of hydrocarbon deposits, so that valuable oil and gas can be recovered from the fewest number of wells.

U.S. Pat. No. 4,476,716 discloses techniques for predicting the likelihood of oil and gas deposits, and specifically discloses the generation of surface temperature data and atmospheric temperature data, and also generation of sub surface temperatures.

U.S. Pat. No. 5,244,483 discloses a technique involving measuring the earth surface temperature at a plurality of locations during a time when ambient conditions are similar to minimize the variability of earth surface temperature and changes in ambient conditions. U.S. Pat. No. 5,281,024 discloses techniques for locating porous and permeable soils having high percolation rates, recognizing that in the summer daytime sunshine, higher surface temperatures are more likely at locations with permeable soils at depth.

In spite of the advances made to accurately locate hydrocarbon deposits on a cost effective basis. There is a gray area of interpretation, and further improvements are necessary to provide more uniformity, so that essentially the same data is obtained when measurements are taken with extended lapses between the measurement periods. Also, more accurate data may be used to more precisely locate and define the size of the hydrocarbon deposits.

SUMMARY OF THE INVENTION

In one embodiment, the method of locating hydrocarbon deposits comprises measuring an earth surface temperature at each of a plurality of locations, and also measuring an absorption coefficient of the earth surface at each of the plurality of locations. Measured earth surface temperature is corrected to obtain a corrected temperature, and the corrected temperatures are compared at the plurality of locations to locate a hydrocarbon deposit. Sky temperatures may also be taken at each of the plurality of locations and used to correct the measured earth surface temperature. In one embodiment, the method included directing a light source having a selected frequency to the earth surface at each of the plurality of locations when measuring the absorption coefficient.

In another embodiment, an apparatus for locating hydrocarbon deposits includes a first sensor for measuring the earth surface temperature at each of a plurality of locations, and a second sensor for measuring absorption coefficient of the earth surface at each of the plurality of locations. A computer is provided for correcting the earth surface temperature to a corrected temperature as a function of the measured absorption coefficient at each of the plurality of locations and outputs corrected temperature data. The light source is provided for directing light rays of a selected frequency onto the earth surface.

These and further features and advantages of the present invention will become apparent from the following detailed description, wherein reference is made to the figures in the accompanying drawings.

BRIEF DESCRIPTION OF THE DRAWINGS

FIG. 1 further illustrates a light source for directing rays onto the earth surface at each of the plurality of locations, and a computer for correcting the measured earth surface temperature.

DESCRIPTION OF THE PREFERRED EMBODIMENTS

Figure 1:
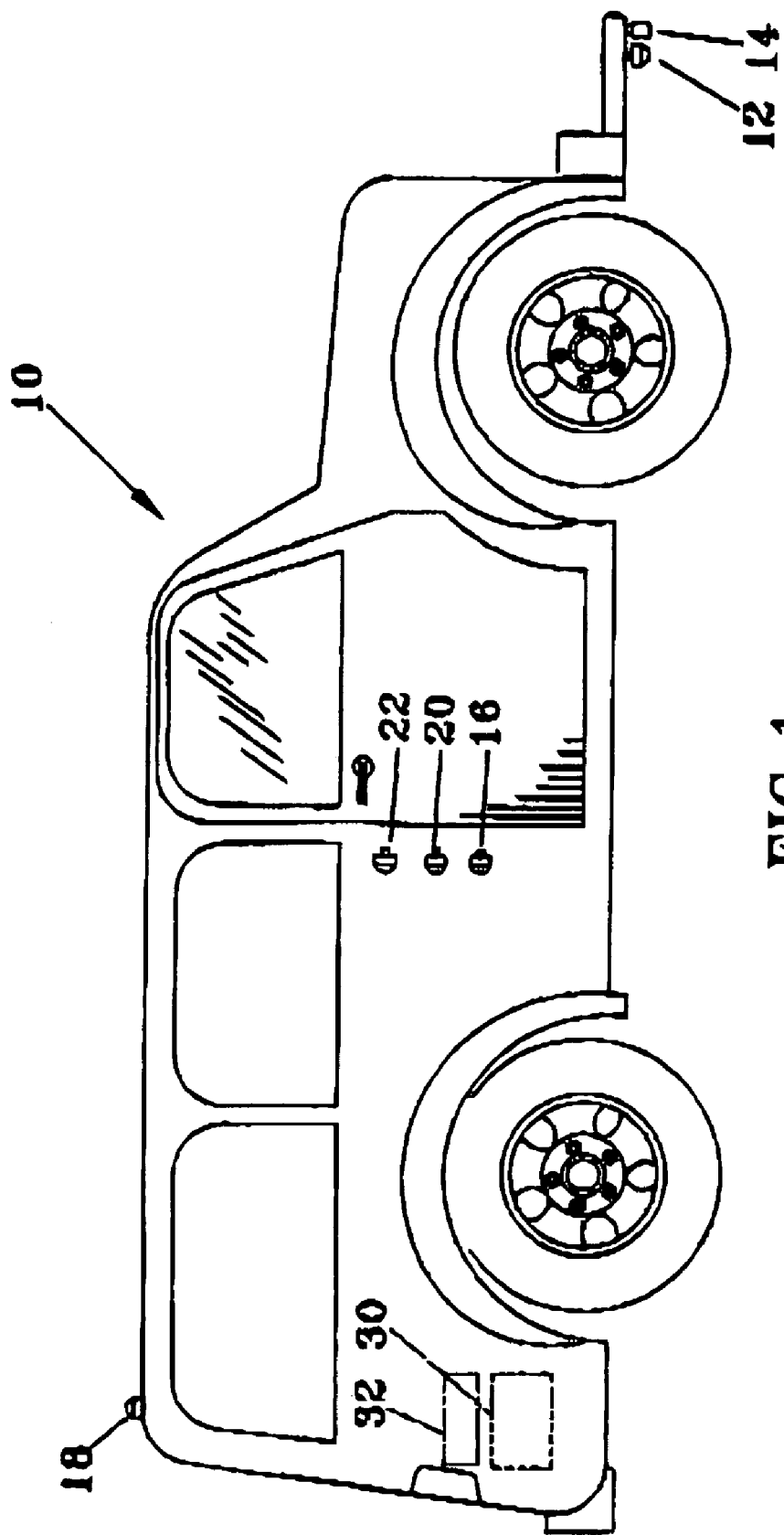
FIG. 1 illustrates a portion of a land vehicle including a sensor for measuring the earth surface temperature at each of a plurality of locations, and another sensor for measuring the absorption coefficient of the earth surface at each of the plurality of locations.

When mapping earth surface temperatures over a period of time within a selected area having a plurality of locations, it is important to provide a technique so that common comparison runs will produce substantially the same results. The atmospheric environment can be expected to slowly change during a series of measurements, although the effects of such changes are generally quite limited and do not significantly affect the interpretive process. If desired, sensors can be used for generating atmospheric data and in response readings corrected due to changing environmental effects may be obtained, as explained below.

Solar heating of the earth surface depends on the surface material's ability to absorb solar energy and the amount of energy presented to the target. Dark materials absorb more and reflect less of the sunrays than do light materials. Surface measurements on an asphalt surface may thus be expected to be higher than surface measurements on an adjacent gravel surface. Unless a correction is made, surfaces that absorb solar energy at a lower rate and thus exhibit lower surface temperatures could mistakenly be preferentially considered as prospective hydrocarbon exploration sites. Uniformity of incident solar energy also becomes a consideration. Daytime surveying on a tree-lined road that provides alternate shade patterns on the road surface may present significant problems to generating meaningful data. Radical changes in the composition of the earth surface due to changes in vegetation, soil type and coloration, water content, and in some cases road surface changes, occur within several feet of each other, and may occur hundreds of times within a mile. The problem of solar absorption becomes less of an issue at extreme earth latitudes during the winter season because of reduced daylight.

Surveys made during the daylight hours do not require artificial light source, but must rely on initial sensitivity settings using solar energy as a source and assume that the energy impinging the sensor's target area remains fairly uniform and at a constant angle of impingement. The target area also cannot be intermittently shaded by the survey vehicle.

Surveys using surface vehicles generally obtain reliable data when traveling at any legal speed, generally between 35 and 70 mph. At these speeds, the effects of change in ambient near surface air temperatures are minimal. Surveys made during the immediate predawn periods are preferred, since the condition of dynamic equilibrium of the earth surface is achieved with a maximum time for solar effects to dissipate.

For the embodiment as shown in FIG. 1, a conventional land vehicle 10 is used to support the light source 12 and the various sensors discussed above. More particularly, FIG. 1 illustrates a solar absorption sensor 14 adjacent the light source 12, an earth surface temperature sensor 16, a sky temperature sensor 18, an ambient temperature sensor 20, and an air humidity level sensor 22. The sensor 14 is designed to effectively accept only wavelengths resulting from solar radiation of the earth surface, and preferably a sensor which is responsive only to wavelengths from about 8 to about 14 microns. One of the sensors that exhibits this quality is a synthetic sapphire sensor.

A computer 30 is provided for recording each measurement as a function of location, and optionally for processing data to make the corrections to the measured surface temperature, as disclosed herein, and outputting results with printer 32. In other embodiments, a separate base computer and a printer may be provided for data processing and display operations, and the computer 30 merely used for recording the data. The computer and the printer preferably output corrected surface temperature data as a function of geographic location of the measurement when taken, so that a plot of surface temperature as a function of distance provides meaningful information to determine the extent of the hydrocarbon deposit.

In another embodiment, a plane may be used to take these measurements. Planes or helicopters may fly several hundred feet above the ground surface at a relatively low speed of from 25 to 55 mph. Solar absorption surveys conducted by aircraft and performed during the daylight hours may be used to normalize predawn infrared survey values. Along with solar absorption data, surface temperature and sky temperature may also be recorded at each of the plurality of locations. Measurements taken from a plane or a land vehicle may be taken during the daytime, although more accurate absorption coefficient measurements likely will be taken at night, since the light source is constant.

The purpose of the solar absorption measurements is to remove the effects of differences in solar heating of the earth materials to permit a better determination of earth heat flow and a prediction of the surface temperature free from differential solar absorption effects. A correction factor should recognize that a rough surface tends to absorb more radiation than a smooth one. Increased reflection produces decreased absorption and thus cooler target surfaces. Oil and gas deposits are recognized by the reduced heat flow from within the earth over such deposits, resulting in reduced earth surface temperature.

The method of the invention thus corrects recorded surface temperatures at locations exhibiting measured variations in solar absorption. Since hydrocarbon deposits generally extend for a distance of a mile or more, the more productive fields can be located by a plot of measurements as a function of distance. Using instruments that effectively accept only wavelengths that vary from about 8 to about 14 microns, the sensor measures radiation emitted by the surface as a consequence of its temperature.

Most solar energy wavelengths are in the range of from about 0.2 to about 3.2 microns. Solar energy absorbed by the target is reradiated at wavelengths related to surface temperature according to well-recognized charts. By measuring and comparing the amount of solar wavelength energy emitted from the surface as a result of a uniform intensity light source, measured surface temperature values may be corrected to provide a more accurate comparison of data to locate the location and boundaries of the hydrocarbon field. Over short earth surface distances, after removing diurnal effects, the measured surface temperatures can be corrected for variations in solar absorption.

Measured temperatures at locations exhibiting high absorption are collected or normalized downward, while measurements of the low absorption areas are corrected upward. Hydrocarbon deposits that are worthy of exploration are generally quite large with substantially uniform overlying negative temperature surface anomalies.

Although specific embodiments of the invention have been described herein in some detail, this has been done solely for the purposes of explaining the various aspects of the invention, and is not intended to limit the scope of the invention as defined in the claims which follow. Those skilled in the art will understand that the embodiment shown and described is exemplary, and various other substitutions, alterations and modifications, including but not limited to those design alternatives specifically discussed herein, may be made in the practice of the invention without departing from its scope.

What is claimed is:

1. A method of locating hydrocarbon deposits, comprising:
   measuring an earth surface temperature at each of a plurality of locations;
   measuring a solar absorption coefficient of the earth surface at each of the plurality of locations;
   correcting the measured earth surface temperature in response to changes in measured absorption coefficients to obtain a corrected temperature; and
   comparing the corrected temperatures at the plurality of locations to locate a hydrocarbon deposit.

2. A method as defined in claim 1, further comprising:
   mapping the corrected temperatures as a function of a geographic position of the plurality of locations.

3. A method as defined in claim 1, further comprising:
   measuring a sky temperature above each of the plurality of locations; and
   correcting the measured earth surface temperature as a function of the measured sky temperature to obtain the corrected temperature.

4. A method as defined in claim 3, wherein the sky temperature is measured at each location simultaneously with the measurement of the earth surface temperature.

5. A method as defined in claim 1, further comprising:
   measuring ambient air temperature at each of the plurality of locations; and
   correcting the measured earth surface temperature as a function of the measured ambient air temperature.

6. A method as defined in claim 1, further comprising:
   measuring air humidity levels at each of the plurality of locations; and
   correcting the measured earth surface temperatures a function of the measured air humidity levels.

7. A method as defined in claim 1, wherein the earth surface absorption coefficients are measured at night.

8. A method as defined in claim 1, further comprising:
   directing a light source having a selected frequency to the earth surface at each of the plurality of locations when measuring the absorption coefficient.

9. A method as defined in claim 8, wherein the light source is mounted on a land vehicle.

10. A method as defined in claim 1, further comprising:
    utilizing a sensor at substantially a fixed location above the earth surface to measure the absorption coefficient.

11. Apparatus for locating hydrocarbon deposits, comprising:
- a first sensor for measuring the earth surface temperature at each of a plurality of locations;
- a second sensor for measuring a solar absorption coefficient of the earth surface at each of the plurality of locations;
- a computer for correcting the measured earth surface temperature to a corrected temperature as a function of the measured absorption coefficient at each of the plurality of locations and outputting corrected temperature data.

12. An apparatus as defined in claim 11, further comprising:
- providing a light source for directing light rays of a selected frequency onto the earth surface at each of the plurality of locations.

13. An apparatus as defined in claim 12, wherein the light source is a tungsten filament bulb having a light frequency range from about 0.2 to about 3.2 microns.

14. An apparatus as defined in claim 12, wherein the light source is mounted on a vehicle.

15. An apparatus as defined in claim 11, wherein the second sensor is responsive only to wavelengths from about 8 to about 14 microns.

16. An apparatus as defined in claim 11, further comprising:
- a third sensor for measuring sky temperature at each of the plurality of locations; and
- the computer outputs the corrected temperature data as a function of the measured sky temperature.

17. An apparatus as defined in claim 11, further comprising:
- an ambient air temperature sensor for measuring ambient air temperature at each of the plurality of locations; and
- the computer outputs the corrected temperature data as a function of the measured ambient air temperature.

18. An apparatus as defined in claim 11, further comprising:
- an air humidity sensor for sensing air humidity at each of the plurality of locations; and
- the computer outputs the corrected temperature signal as a function of the air humidity measurements.

19. A method of locating hydrocarbon deposits, comprising:
- measuring an earth surface temperature at each of a plurality of locations;
- directing a light source having a selected frequency to the earth surface at each of the plurality of locations while measuring the absorption coefficient;
- measuring a solar absorption coefficient of the earth surface at each of the plurality of locations;
- correcting the measured earth surface temperature as a function of the measured absorption coefficient to obtain a corrected temperature; and
- comparing the corrected temperatures at the plurality of locations to locate a hydrocarbon deposit.

20. A method as defined in claim 19, further comprising:
- mapping the corrected temperatures as a function of a geographic position of the plurality of locations.

* * * * *